United States Patent [19]

Bockman et al.

[11] Patent Number: 5,686,116
[45] Date of Patent: Nov. 11, 1997

[54] METHODS OF ENHANCING REPAIR, HEALING AND AUGMENTATION OF BONE IMPLANTS

[75] Inventors: Richard Bockman, New York, N.Y.; Peter Guidon, Cranford, N.J.

[73] Assignee: New York Society For The Relief Of The Ruptured and Crippled, Maintaining The Hospital for Special Surgery, New York, N.Y.

[21] Appl. No.: 461,724

[22] Filed: Jun. 5, 1995

Related U.S. Application Data

[63] Continuation-in-part of Ser. No. 430,142, Apr. 26, 1995, Pat. No. 5,556,645, which is a continuation of Ser. No. 910,118, Sep. 14, 1992, abandoned, which is a continuation-in-part of Ser. No. 464,361, Jan. 1, 1990, abandoned.

[51] Int. Cl.$^6$ .................. A61K 33/24; A61K 38/16; A61K 31/28
[52] U.S. Cl. .................. 424/650; 514/8; 514/492
[58] Field of Search .................. 424/650; 514/492, 514/8

[56] References Cited

U.S. PATENT DOCUMENTS

| | | | |
|---|---|---|---|
| 4,529,593 | 7/1985 | Warrell, Jr. et al. | 424/650 |
| 4,686,104 | 8/1987 | Bockman et al. | 424/649 |
| 4,704,277 | 11/1987 | Bockman et al. | 424/650 |
| 4,882,166 | 11/1989 | Graham et al. | 424/462 |

FOREIGN PATENT DOCUMENTS

62230648A  10/1987  Japan .

OTHER PUBLICATIONS

Quarles et al., 1991, Endocrinol. 128:3144–3151.
Quarles et al., 1990, J. Bone and Mineral Res. 5:625–635.
Qualres et al., 1989, J. Clin. Invest. 83:1644–1650.
Bergkvist et al., 1989, New Engl. J. Med. 321:293–297.
Ernst et al., 1989, Endocrinol. 125:825–833.
Kleerekoper et al., 1989, J. Bone and Min. Res. 4:S376.
ten Dijke and Iwata, 1989, Bio/Technol. 7:793–798.
Warrell and Bockman, 1989, in *Important Advances in Oncology* 1989, J.B. Lippencott Co., New York, pp. 205–220.
Repo et al., 1988, Calcified Tissue International 43:300–306.
Quarles et al., 1988, J. Clin. Invest. 81:1056–1066.
Bockman et al., 1987, Clinical Res. 35:620.
Centrella et al., 1987, J. Biol. Chem. 262:2869–2874.
Noda and Rodan, 1987, J. Cell. Physiol. 133:426–437.
Robey et al., 1987, J. Cell. Biol. 105:457–463.
Sporn et al., 1987, J. Cell Biol. 105:1039–1045.
Seyedin et al., 1986, J. Biol. Chem. 261:5693–5695.
Kream et al., 1985, Endocrinol. 296–302.
Warrell et al., 1984, J. Clin. Invest. 73:1487–1490.
Feinberg and Fogelstein, 1983, Biochemistry 132:6–13.
Rodan and Martin, 1981, Calcified Tissue International 33:349–351.
Majeska et al., 1980, Endocrinol 107:1494–1503.
Chirgwin et al., 1979, Biochemistry 18: 5294–5299.
Lindsay et al., May 15, 1976, the Lancet, pp. 1038–1040.
Schenk et al., 1973., Calcified Tissue Res. 11: 196–214.
Jowsey et al., 1968, J. Clin. Endocrinol. 28:869–874.
Lowry et al., 1954, J. Biol. Chem. 207:19–37.
Schmidt et al., "Teaninatier of new bone growth on aluminium oxide implants . . . " see abstract.
Windolz et al., *The Merck Indes*, 10th Ed. p. 1369 ab. No. 9393.

*Primary Examiner*—Kevin E. Weddington
*Attorney, Agent, or Firm*—Brumbaugh, Graves, Donohue & Raymond

[57] ABSTRACT

Tissue and organ repair, healing and augmentation are enhanced by administering pharmaceutically acceptable group IIIa element-containing compounds in amounts sufficient to provide therapeutic levels of the elements. Group IIIa element-containing compounds mimic the beneficial biological effects of endogenous growth factors to induce cells responsible for repair, healing and augmentation of tissues and organs. Group IIIa element-containing compounds are suitable for a variety of applications such as wound healing, bone fracture repair, treatment of dermatologic conditions and successful bonding of implanted tissue grafts and prostheses.

9 Claims, No Drawings

METHODS OF ENHANCING REPAIR, HEALING AND AUGMENTATION OF BONE IMPLANTS

SPECIFICATION

This application is a continuation-in-part of U.S. Ser. No. 08/430,142; now U.S. Pat. No. 5,556,645, filed Apr. 26, 1995, which is a continuation of U.S. Ser. No. 07/910,118, filed Sep. 14, 1992 (abandoned), which is a continuation-in-part of U.S. Ser. No. 07/464,361, filed Jan. 1, 1990 (abandoned).

This invention was made in part with support under grant NCI-CA-38645 awarded by the National Institutes of Health. The Government has certain rights in the invention.

FIELD OF THE INVENTION

The present invention relates to the use of group IIIa element-containing compounds in biological applications, including those previously indicated for transforming growth factor β (TGFβ). For example, the present invention includes the use of group IIIa element-containing compounds to enhance tissue and organ repair, healing and augmentation. As used herein, the phrase group IIIa element-containing compounds refers to compounds containing the group IIIa elements boron, aluminum, gallium, indium, or thallium. Group IIIa element-containing compounds mimic the beneficial activities of the natural repair factor, TGFβ. As used herein and in the claims, the word TGFβ refers to a family of endogenous growth factors such as TGFβ-1, TGFβ-2, TGFβ-3 and bone morphogenetic proteins (BMP).

BACKGROUND OF THE INVENTION

Naturally produced substances have been discovered which promote repair, healing and augmentation of tissues and organs. Such substances have been termed "growth factors". Growth factors, usually proteins, initiate programs of differentiation and/or development within an organism. When referring to tissue repair, the appellation "growth factor" is a misnomer. Confusion in separating the biological processes of growth from the processes involved in repair, healing and augmentation is often caused by the use of the term "growth factors" to describe these proteins. Repair, healing and augmentation, as discussed in detail below, are distinct biological activities and are clearly distinguishable from growth. Growth in the biological sense is defined as progressive development from a lower or simpler to a higher or more complex form of organization. Tissues and organs "grow" from a few similar appearing cells to a complex organized structure, such as a kidney or an eye. For clarity, organs are defined as functional units of the body containing multiple cell types. Examples of organs include, for instance, kidneys, eyes, the liver, the heart, bone, skin and cartilage. Tissues are defined as functional units of the body that are made up of almost an entirely single cell type. For instance, connective and support tissues are derived from and comprised of almost entirely a single cell type, e.g. fibroblast or muscle cell.

Growth factors can stimulate wound healing. The process of wound healing begins immediately following surface lesions or after skin proteins become exposed to radiation, chemical damage or extreme temperatures. Wound healing requires close control of degradative and regenerative processes, involving numerous cell types and complex interactions between multiple biochemical cascades. Growth factors released in the traumatized area stimulate and promote the following: 1) cell migration into the wound area (chemotaxis); 2) proliferation of epithelial cells, muscle cells, endothelial cells, blood cells and fibroblasts (mitogenesis); 3) formation of new blood vessels (angiogenesis); and 4) matrix formation and remodeling of the affected region including re-epithelization by keratinocytes. Studies on animals have shown that exogenously added growth factors can accelerate the normal healing process, and studies on humans have shown that growth factors can heal previously incurable wounds. Factors capable of enhancing wound healing are particularly important in treatment of patients with chronic wounds which may require daily treatment, represent a constant source of pain to the patient, may lead to life threatening infection and are a significant medical expense. Chronic wounds are those which are slow-healing or which do not heal at all and are common to diabetics, cancer patients and those confined to bed for long periods of time. Treatment of chronic wounds may consume up to $4 billion per year in medical expenses in the United States alone. Skerrett, "'Matrix Algebra' Heals Life's Wounds", Science, 252:1064–1066 (1991).

Despite their beneficial effect on bone, cartilage, skin and connective and support tissue, the use of growth factors poses several problems. Growth factors, when systemically administered, affect non-target organs and may therefore elicit a variety of adverse side effects. For instance, one recent article expressed the opinion that TGFβ may contribute to the renal lesions found in glomerulonephritis, the leading cause of kidney failure in people with diseases such as lupus, diabetes and hypertension. Skerrett (1991). Further problems with growth factors are their instability and tendency to break down once purified and stored for therapeutic use. Moreover, many of the amino acid sequences of growth factors vary between species and are consequently recognized as foreign by dissimilar, or heterologous, species. There is thus the constant danger of eliciting an immune response upon administration of heterologous growth factors. Furthermore, there is no evidence that parenterally administered growth factors target to bone, cartilage, skin and connective and support tissues. Parenteral administration refers to routes such as intravenous, intramuscular, intraperitoneal and subcutaneous.

As proteins, growth factors are not suitable for oral administration, since they are digested and destroyed before entering the blood stream. Growth factors cannot be satisfactorily administered as topical ointments except for skin wounds, because they are only slowly absorbed by the body and subsequently break down rapidly. Because of these and other problems, growth factors are typically administered intravenously. Since naturally occurring growth factors can alter the function of many organs and tissues of the body, intravenous administration of growth factors affects many non-target organs. A therapeutically effective compound that directly targets bone, cartilage, skin and connective and support tissues when parenterally administered or that can be directly applied to the tissues or organs that need to be repaired, healed or augmented is highly preferred to currently available naturally occurring growth factors.

TGFβ belongs to a family of growth factors that produce multiple biological effects, including mitogenesis, growth regulation, regulation of cartilage and bone formation, chemotaxis and induction or inhibition of cell differentiation, depending on the tissue or cell type and the presence or absence of other growth factors. Most of the published work on TGFβ relates to its wound healing capabilities. However, TGFβ plays other physiological roles, as shown by the fact that it is known to be contained and produced within bone. Seyedin et al., "Cartilage-Inducing Factor", J. Biol. Chem., 261:5693-5695 (1986); and Robey et al., "Factor-Type β (TGFβ) in vitro", J. Cell Biol., 105:457-463 (1987). TGFβ will enhance bone formation. Sporn et al., "Some Recent Advances in the Chemistry and Biology of Transforming Growth Factor-β", J. Cell Biol., 105:1039-1045 (1987). Other members of the TGFβ family of growth factors, notably BMP, have also been shown to enhance bone formation. Wozney et al., "Novel Regulators of Bone Formation: Molecular Clones and Activities", Science, 242:1528-1533 (1988).

Recent studies with purified cell membranes have shown that gallium nitrate $(Ga(NO_3)_3)$ can block the transport of hydrogen atoms across osteoclast cell membranes. This hydrogen atom transport would otherwise lead to the dissolution of the mineral matrix of bone, thereby releasing calcium ions into the blood. Although TGFβ affects bone repair, healing and augmentation, it has not been shown to block transport of hydrogen atoms across osteoclast cell membranes. In fact, TGFβ has not been demonstrated to be a clinically effective antiresorptive agent capable of preventing accelerated bone breakdown and disordered calcium homeostasis. Indeed, unlike previously shown activity of gallium nitrate, TGFβ inhibits the differentiation and proliferation of osteoclastic cells, leading to decreased osteoclast cell numbers. Chenu et al., "Transforming Growth Factor Beta Inhibits Formation of Osteoclast-Like Cells in Long-Term Human Marrow Cultures", Proc. Natl. Acad. Sci. USA, 85:5683-5687 (1988). By contrast, rats treated with gallium nitrate have normal or increased numbers of osteoclasts. Cournot-Witmer et al., "Bone Modelling in Gallium Nitrate Treated Rats", Calcif. Tis. Int., 40:270-275 (1987).

Prior patents refer to conditions affecting the mineral (non-living), inorganic component of bone. U.S. Pat. Nos. 4,529,593 (Warrell and Bockman), 4,686,104 (Bockman et al.), and 4,704,277 (Bockman et al.) describe methods of preventing excessive loss of calcium from human bone by the administration of gallium nitrate. These patents describe the ability of gallium nitrate to inhibit bone resorption (breakdown) so as to prevent disordered calcium homeostasis.

There is no direct relationship between the deposition of the mineral component of bone and biologic bone repair, healing and augmentation. The mineral component of bone is made up of hydroxyapatite, a crystalline, inorganic complex of calcium and phosphate. Hydroxyapatite crystals "grow" in size in the physical process of accretion (i.e., addition) of new atoms of calcium and phosphate. Calcium accretion onto crystalline hydroxyapatite of bone is a passive physical-chemical process that does not require living cells. The synthesis of new matrix components which requires living cells, the activation of specific genes and the de novo synthesis of proteins from organic elements, is unrelated to calcium accretion. The basic building blocks for matrix synthesis come from living cells and have, for the most part, been synthesized de novo by those cells. Disorders of calcium homeostasis, therefore, affect only the inorganic matrix of bone and are unrelated to repair, healing and augumentation in the biologic sense. Mechanisms involved in repair, healing and augmentation of the organic matrix of bone, cartilage, skin and connective and support tissues represent biologic processes that are different and distinct from mechanisms involved in calcium accretion.

Several pharmaceutical agents, including cisplatin, mithramycin, calcitonin and bisphosphonates, have been shown to inhibit resorption of bone mineral matrix. None of these agents, however, have a proven beneficial effect on bone formation or wound healing. Cisplatin and mithramycin are cytotoxic agents which, when injected parenterally, act by killing the cells responsible for tissue breakdown, as well as those responsible for tissue formation. Calcitonin, a naturally produced hormone, transiently inhibits the activity of bone-resorbing cells (osteoclasts) to prevent bone breakdown. Calcitonin increases excretion of calcium by the kidneys and thus accelerates calcium loss from the body.

Bisphosphonates are a class of synthetic compounds that inhibit bone resorption. Etidronate (EHDP) is currently the only bisphosphonate approved for use in the United States. Osteoporosis patients who have been treated with EHDP, however, have shown a 50% increase in vertebral fracture rates in the third year. See, e.g., "Update: Bisphosphonates Editronate evaluated by FDA", Lunar News, March 1991. The possible ineffectiveness of EHDP over long-term treatment tends to indicate that agents that inhibit bone resorption do not strengthen bone in a clinically significant manner, and in fact, may tend to weaken bone. Further, EHDP inhibits matrix-forming cells. Schenk et al., "Effect of Ethane 1-hydroxy-1, 1-diphosphate (EHDP) and Dichloromethylene Diphosphonate ($Cl_2MDP$) on the Calcification and Resorption of Cartilage and Bone in the Tibial Epiphysis and Metaphysis of Rats", Calcif. Tis. Res., 11:196-214 (1973).

Fluoride-containing salts have been extensively tested for their effects on matrix-forming cells. Treatment with fluoride, however, results in the production of a highly abnormal (woven-type) bone matrix structure. Such fluoride-induced bone is weaker than normal bone. Jowsey et al., "Some Results of the Effect of Fluoride on Bone Tissue in Osteoporosis", J. Clin. Endocrinol., 28:869-874 (1968). Indeed, a recently completed study showed that fluoride did not significantly reduce skeletal fractures in osteoporotic women. Kleerekoper et al., "Continuous Sodium Fluoride Therapy Does Not Reduce Vertebral Fracture Rate in Postmenopausal Osteoporosis", J. Bone and Min. Res., 4:S376 (1989).

Estrogen replacement therapy has resulted in increased bone mass in estrogen-deficient, post-menopausal women. Lindsay et al., "Long-Term Prevention of Postmenopausal Osteoporosis by Estrogen Treatment", Lancet, 1:1038-1041 (1976). Estrogen directly affects bone-forming cells to increase matrix elements, such as collagen, and to increase an endogenous growth factor, insulin-like growth factor-I (IGF-1). Ernst et al., "Estradiol Effects on Proliferation, Messenger RNA for Collagen and Insulin-like Growth Factor-I, and Parathyroid Hormone-Stimulated Adenylate Cyclase Activity on Osteoblastic Cells from Calvariae and Long Bones", Endocrinol., 125:825-833 (1989). However, the benefits of estrogen treatment are limited to perimenopausal women, those women who are about to enter or who have entered menopause. Furthermore, estrogen treatment is associated with increased risk of uterine and breast cancer. Bergkvist et al., "The Risk of Breast Cancer After Estrogen and Estrogen-Progestin Replacement", N. E. J. Med., 321:293-297 (1989).

In summary, exogenous growth factors, while capable of inducing synthesis of new matrix components in a manner that simulates natural, normal, conditions of repair, healing and augmentation of organs and tissues, have proven to be difficult to administer and tend to cause side effects. Further, various pharmaceutical agents have proven unsuccessful in inducing synthesis of new matrix components in a manner that simulates natural, normal, conditions of repair, healing and augmentation of organs and tissues.

It is therefore an object of the present invention to provide methods and compositions for enhancing normal repair, healing and augmentation of bone, cartilage, skin and connective and support tissue that can be administered by a variety of routes and are virtually free of side effects.

A further object of this invention is to provide a method of enhancing normal repair, healing and augmentation of tissues and organs wherein the therapeutic agent: a) does not breakdown once purified and stored; b) is not destroyed by digestive processes; c) does not cause adverse immunological effects; and d) does not increase bone fracture rates.

SUMMARY OF THE INVENTION

The present invention includes but is not limited to methods of enhancing normal repair, healing and augmentation of bone, cartilage, skin, and connective and support tissue, by administering group IIIa element-containing compounds to a subject with a wound, tear, break, or deficiency of matrix components in bone and cartilage, skin, and connective and support tissues. It has now been found that group IIIa element-containing compounds mimic the beneficial biological effects of TGFβ, but not the detrimental side effects of TGFβ, and are thus preferable for use in any indication in which TGFβ is used. The present invention also includes pharmaceutically acceptable compositions suitable for administering group IIIa element-containing compounds in an amount sufficient to cause the selective synthesis of matrix components so as to enhance repair, healing and augmentation of the strength and appearance of bone, cartilage, skin and connective and support tissues.

DETAILED DESCRIPTION OF THE INVENTION

Pharmaceutically acceptable group IIIa element-containing compounds have been found to mimic the molecular action of naturally occurring TGFβ. Boron, aluminum, gallium, indium and thallium belong to the group IIIa elements and are thus encompassed by the present invention. In a preferred embodiment of the present invention, the group IIIa element-containing compound is any therapeutically effective, pharmaceutically acceptable composition containing gallium. In another preferred embodiment of the present invention, the group IIIa element-containing compound is any therapeutically effective, pharmaceutically acceptable composition containing indium.

In particular, results have been obtained with gallium nitrate and indium nitrate treated bone, cartilage, skin and connective and support tissues, indicating that the mechanisms of action of gallium, indium and other group IIIa elements are similar to that of TGFβ with respect to enhanced normal tissue and organ repair, healing and augmentation. The results obtained indicate that group IIIa element-containing compounds induce the synthesis of both mRNA and proteins involved in tissue and organ repair, healing and augmentation. Group IIIa element-containing compounds are unique in that they are pharmaceutically acceptable compounds which are relatively inert, stable, do not evoke an immune response, are not subject to contamination as are purified biological compounds, can be administered in a wide variety of ways, and cause few side effects. The compounds are not antigenic and demonstrate a preference to localize to bone, cartilage, skin and connective and support tissues.

The active ingredient in group IIIa element-containing compounds is the group IIIa element and not any accompanying salt. Therefore any pharmaceutically acceptable compound which provides adequate blood and tissue levels of elemental boron, aluminum, gallium, indium or thallium proximate to the site of injury can be used according to the present invention. Gallium nitrate has been used in the following examples and is representative of all pharmaceutically acceptable group IIIa element-containing compounds capable of providing therapeutically effective levels of elemental boron, aluminum, gallium, indium or thallium for uptake by the patient. Suitable group IIIa element-containing compounds include but are not limited to gallium-containing compounds, such as gallium nitrate, 9allium phosphate, gallium citrate, gallium chloride, gallium fluoride, gallium carbonate, gallium formate, gallium acetate, gallium tartrate, gallium maltol, gallium oxalate, gallium oxide, hydrated gallium oxide, coordination complexes of gallium and protein bound gallium, indium or thallium compounds and the equivalent compounds for the other group IIIa elements.

Coordination complexes of gallium include but are not limited to gallium pyrones (such as those derived from kojic acid); gallium pyridones (such as desferal); gallium hydroxymates; gallium amino carboxylates or gallium bound oximes (such as 8-hydroxy quinolone) and the equivalent complexes for the other group IIIa elements. Coordination complexes are based on the known coordination chemistry of the group IIIa elements. A coordination compound is an association of metal ion, particularly a transitional element, with other ions or molecules which are called ligands. Together they produce a composite complex compound called a coordination complex. The transitional elements are best known and studied as they have available d-orbital electrons suited to bond with ligands such as $NO_3$, citrate etc.

Proteins, such as transferrin or lactoferrin, are suitable for binding to gallium, indium or thallium and the equivalent compounds for the other group IIIa elements. Proteins are bound to these elements by any means known in the art.

The word "repair", as used herein, means the natural replacement of worn, torn or broken components with newly synthesized components. The word "healing", as used herein, means the returning of torn and broken organs and tissues (wounds) to wholeness. The word "augmentation", as used herein, means increasing what is already whole or intact by the synthesis and incorporation of additional normal tissue or organ components in order to normally increase the size and/or the strength of the tissue or organ.

Natural mechanisms of repair, healing and augmentation are similar for bone and cartilage, skin and connective and support tissues. These will be discussed in turn. The connective and support tissues being discussed include ligaments, muscles, tendons and those tissues, such as the collagen-containing tissues which encapsulate organs. Although repair, healing and augmentation require a complex series of events that are not well defined, it is known that specific, naturally occurring factors are required to achieve these objectives. Such factors are released into the injured area, or migrate into the wound, and stimulate osteoblasts and chondrocytes and odontoblasts in bone and cartilage, fibroblasts and keratinocytes in skin and fibroblasts and muscle cells in connective and support tissues to stimulate matrix formation and remodeling of the wounded area. ten Dijke et al., "Growth Factors for Wound Healing", Bio/Technology, 7:793–798 (1989).

The current invention includes methods by which group IIIa element-containing compounds enhance tissue and organ repair, healing and augmentation. Methods and compositions are provided for enhancing: 1) the normal repair, healing and augmentation of the organic matrix of bone; 2) the attachment and fixation of bone implants and prostheses; 3) the repair, healing and augmentation of cartilage; 4) the attachment and fixation of cartilage implants; 5) the repair, healing and augmentation of skin; 6) the attachment and fixation of skin grafts and skin prostheses; and 7) the attachment of connective and support tissue grafts. The invention further includes compositions for enhancing the normal repair, healing and augmentation of connective and support tissues, bone, cartilage, skin, ligaments, tendons, muscles, and fascia. Skin repair includes the repair of dermatologic disorders (due to damage, injury or aging), and augmentation includes increasing skin fullness for the purpose of removing wrinkles and folds.

From the data presented below, it is evident that group IIIa element-containing compounds mimic the action of the TGFβ in wound healing, repair and augmentation, by directly stimulating the activity of matrix-forming cells and consequently enhancing the formation of matrix components. Matrix-forming cells synthesizing the structural elements of connective and support tissues, bone, cartilage and skin respond to group IIIa element-containing compounds in a manner similar to that of TGFβ. The growth-factor-like effects of the group IIIa element-containing compounds enhance the repair, healing and augmentation of bone and cartilage, skin and connective and support tissues by mimicking the effect of TGFβ on the necessary naturally occurring components that are used in the normal repair, healing and augmentation processes. The mechanisms of repair, healing and augmentation are similar in many respects for man and animals; hence veterinary applications of this invention are also apparent.

Applicant's experimental studies have shown that treatment with group IIIa element-containing compounds initiates a biologic response in bone and cartilage, skin and connective and support tissues which results in a specific pattern of matrix gene expression. Two types of new proteins are synthesized as a consequence of treatment with group IIIa element-containing compounds. The first set of proteins ("early regulatory proteins") instruct the cells within the tissues or organs to make other proteins (matrix proteins in this case) in a specific pattern or temporal sequence. It is the latter set of proteins that replace and restore torn or broken components to render the organ or tissue repaired, whole (healed) or augmented.

Group IIIa element-containing compounds, especially gallium nitrate, in a pharmaceutically acceptable form and at doses far below those known to be cytotoxic have now been found to exert beneficial effects on bone osteoblasts, skin fibroblasts and keratinocytes and on connective and support tissue fibroblast function. In explanted tissues, treatment with group IIIa element-containing compounds has now been shown to enhance the synthesis of new bone matrix elements. In living rats with an induced abnormality in bone formation, group IIIa element-containing compounds have now been shown to normalize osteoblast function. In isolated bone, skin and connective and support tissue cells, group IIIa element-containing compounds have now been shown to enhance synthesis of the components necessary for organ and tissue repair, healing and augmentation. In general, group IIIa element-containing compounds are pharmaceutically acceptable due to their low toxicity in the therapeutic dosage range (see infra), stability and ability to be incorporated into a wide variety of vehicles for numerous routes of administration.

The group IIIa element-containing compounds can be administered alone or in combination with other group IIIa element-containing compounds or growth factors such as TGFβ or any other suitable therapeutic compound, such as antibiotics, proteases and cell adhesion molecules. See e.g. Skerrett, (1991). Suitable growth factors include but are not limited to TGFβ, platelet derived growth factor (PDGF), epidermal growth factor (EGF), BMP and fibroblast growth factor (FGF). The group IIIa element-containing compounds are generally administered with a pharmaceutically acceptable carrier or vehicle therefor. A pharmaceutically acceptable carrier is one that does not cause an adverse physical reaction upon administration and one in which group IIIa element-containing compounds are sufficiently soluble to deliver a therapeutically effective amount of the compound. The therapeutically effective amount and method of administration of the group IIIa element-containing compounds may vary based on the individual patient, the indication being treated and other criteria evident to one of ordinary skill in the art. A therapeutically effective amount of a group IIIa element-containing compound is one sufficient to induce repair, healing or augmentation of a target organ or tissue. The route(s) of administration useful in a particular application are apparent to one of ordinary skill in the art.

Routes of administration include, but are not limited to, topical, transdermal, parenteral, gastrointestinal, transbronchial and transalveolar. Topical administration is accomplished via a topically applied cream, gel, rinse, etc. containing a group IIIa element-containing compound. Transdermal administration is accomplished by application of a cream, rinse, gel, etc. capable of allowing the group IIIa element-containing compound to penetrate the skin and enter the blood stream. Parenteral routes of administration include but are not limited to electrical or direct injection such as intravenous, intramuscular, intraperitoneal or subcutaneous injection. Gastrointestinal routes of administration include but are not limited to ingestion and rectal. Transbronchial and transalveolar routes of administration include but are not limited to inhalation, either via the mouth or intranasally and direct injection into an airway, such as through a tracheotomy.

The present invention also includes compositions of group IIIa element-containing compounds suitable for use in topical application including, but not limited to, pharmaceutically acceptable lotions, liposomal carriers suspended in a suitable base or vehicle, ointments, creams, rinses and gels. Any liquid, pharmaceutically acceptable vehicle in which the group IIIa element-containing compounds are at least minimally dissolved is suitable for topical use in the present invention. The creams, ointments etc. containing group IIIa element-containing compounds can be delivered by dressings, bandages or other similar coverings capable of releasing a therapeutic amount of group IIIa element-containing compounds. Such dressings are placed directly on the wound to promote healing.

The present invention provides compositions suitable for transdermal administration including, but not limited to, pharmaceutically acceptable lotions, suspensions, oils, creams, ointments, rinses, gels and liposomal carriers suspended in a suitable vehicle in which a therapeutically effective amount of group IIIa element-containing compound has been admixed. Such compositions are applied directly to the skin or incorporated into a protective carrier such as a transdermal device (so-called "patch"). Examples of suitable creams, ointments etc. can be found, for instance, in the Physician's Desk Reference. Examples of suitable transdermal devices are described, for instance, in U.S. Pat. No. 4,818,540 (Chien et al.).

The present invention includes compositions of group IIIa element-containing compounds suitable for parenteral administration including, but not limited to, pharmaceutically acceptable sterile isotonic solutions. Such solutions include, but are not limited to, saline and phosphate buffered saline for intravenous, intramuscular, intraperitoneal or subcutaneous injection of group IIIa element-containing compounds.

The present invention includes compositions suitable for gastrointestinal administration including, but not limited to, pharmaceutically acceptable powders, pills or liquids for ingestion and suppositories for rectal administration.

The present invention includes compositions of group IIIa element-containing compounds suitable for transbronchial and transalveolar administration including, but not limited to, various types of pharmaceutically acceptable aerosols for inhalation. An example of a drug administered in the form of an aerosol is pentamidine which is administered to AIDS patients by inhalation to prevent pneumonia caused by *Pneumocystis carnii*.

The present invention further contemplates devices suitable for transbronchial and transalveolar administration of group IIIa element-containing compounds. Such devices include, but are not limited to, atomizers and vaporizers. The present invention also includes devices for electrical or direct injection. Electrical injection, or iontophoresis, is the process of using a small electrical current to drive charged elements, compounds and drugs through the skin for the purpose of delivering the therapeutic compound to the local tissues or to the whole body without breaking the skin.

The above-mentioned compositions are meant to describe, but not limit, the methods of administering the group IIIa element-containing compounds of the invention. The methods of producing the various compositions are within the ability of one skilled in the art and are not described in detail here.

The methods of producing suitable devices for injection, topical application, atomizers and vaporizers are known in the art and will not be described in detail.

According to the present invention, therapeutic levels of pharmaceutically acceptable group IIIa element-containing compounds are administered to the patient in order to obtain the beneficial effects of group IIIa element-containing compounds. The therapeutic amount, as well as the method of administration, may vary according to the disorder being treated, its severity, the age of the patient and other factors evident to one skilled in the art. Typically, therapeutic levels are attained when the group IIIa element is present in a steady state concentration in blood of about 1.0 to 150 μM with a preferred range of about 1.0 to 50 μM or, when the group IIIa element is present in tissues, at a steady state of concentration of about 1.0 to 1000 ng/mg dry weight of tissue with a preferred range of about 1.0 to 500 ng/mg dry weight of tissue. If group IIIa element-containing compounds are applied proximate to the site of injury, however, lower levels of elemental boron, aluminum, gallium, indium or thallium may be maintained within the body. For instance the effective concentration of the group IIIa element needed at the site of injury would be about 0.25 to 100 μM, thereby resulting in limited levels of group IIIa element-containing compounds in the blood and viscera since absorption from the site would be relatively insignificant.

A further advantage of the present invention is that group IIIa element-containing compounds can be applied directly or proximate to the site of injury. The only previously known route of administration of gallium-containing compounds had been parenteral, which necessitated hospitalization and the administration of relatively high concentrations of gallium-containing compounds. It has now been found that group IIIa element-containing compounds can be applied to the site of injury resulting in lower serum levels and less exposure to non-involved organs and tissues. Such direct application increases the effectiveness at the site of injury, thus decreasing the risk of side effects.

Bone

Bone provides an ideal model system in which mechanisms of repair, healing and augmentation can be examined in detail. Such mechanisms in bone have been studied extensively and are easily manipulated. Bone is maintained and repaired by matrix-producing cells known as osteoblasts. Osteoblasts are derived from local mesenchymal (stromal) precursors which differentiate into osteoblasts.

The bone-forming osteoblasts produce two types of matrices. The first is an organic matrix made predominantly from the structural protein collagen; the second is a mineral matrix made up of calcium and phosphate found almost exclusively as hydroxyapatite in the form of fine crystalline particles distributed selectively along the collagen fibers. The organic collagen matrix and the orientation of the proteins in that matrix determine the architectural and structural integrity of bone. The normal lamellar pattern of the collagen fibrils provides the tensile strength of bone.

New collagen synthesis is necessary although not sufficient for bone, cartilage, skin, support and connective tissue repair, healing and augmentation. Each of these will be discussed in turn with respect to treatment with group IIIa element-containing compounds.

In bone and cartilage, collagen synthesis is required for injury repair, the successful bonding of grafts and prosthetic devices and for the increase of organic mass (augmentation), all of which yield increased bone strength. Several non-collagen molecules synthesized by the osteoblast, including osteonectin, osteopontin and osteocalcin, are thought to be additionally necessary for ordered bone matrix formation. It is the mineral matrix that provides the stiffness and compressive strength of bone. The normal mineral matrix of bone can only form after the organic (collagen) matrix has been formed. Therefore, it is the regulation of bone collagen synthesis by the osteoblast that determines the initial pattern of bone mineralization. The regulation of calcium movement into and out of the mineral compartment of bone is a critical aspect of calcium homeostasis in the body. Calcium homeostasis is regulated by many factors both within and from outside bone and is an entirely separate process from the synthesis of the organic matrix of bone by osteoblasts. In addition to the proteins used in the synthesis of the organic matrix, the osteoblast produces specific enzymes. One such enzyme, bone alkaline phosphatase, is a reliable indicator of osteoblast activity.

Bone formation, repair, healing and augmentation by osteoblasts are complicated processes that are not fully understood. Recent studies have provided important new information about the molecular events leading to normal bone repair. In particular, naturally occurring growth factors have been identified within bone that elicit a specific pattern of protein synthetic activity by osteoblasts resulting in enhanced bone repair, healing and augmentation. TGFβ, found in bone, stimulates expression of genes in osteoblasts leading to synthesis of regulatory proteins which in turn activate other genes responsible for normal synthesis and integration of new bone components into existing bone.

Centrella et al., "Transforming Growth Factor-β is a Bifunctional Regulator of Replication and Collagen Synthesis in Osteoblast-Enriched Cell Cultures From Fetal Rat Bone", J. Biol. Chem., 262:2869–2874 (1987); and Noda et al., "Type Beta Transforming Growth Factor Regulation of Alkaline Phosphatase Expression and Other Phenotype-related MRNA'S in Osteoblastic Rat Osteosarcoma Cells", J. Physiol., 133:426–437 (1987). Coincidentally, TGFβ decreases the synthesis of specific proteases (e.g. particular enzymes) that normally break down matrix proteins. Sporn et al. (1987). The coordinate activities induced by TGFβ promote the accumulation of matrix elements and explain the improved repair, healing and augmentation seen in TGFβ treated animals. Sporn et al. (1987).

A second major class of bone cells, osteoclasts, are derived from unique precursors in the bone marrow. Osteoclasts are able to dissolve both the mineral and organic matrices of bone. Under normal conditions, the actions of osteoblasts and osteoclasts are "coupled" such that osteoclasts "model or remodel" bone synthesized by osteoblasts into a structure best designed to provide support to the body. In certain pathologic conditions, osteoclast-mediated resorption is not regulated by osteoblasts but is driven by cancer cells, infecting organisms or the host's immune cells. In those disease conditions, resorption of bone far exceeds bone formation. Such accelerated osteoclastic activity leads to excessive release of calcium from the inorganic mineral in bone, with a concomitant net loss of skeletal mass, often with an attendant disturbance in calcium homeostasis in the form of elevated blood levels of calcium.

Gallium nitrate has been shown to be effective in blocking osteoclastic bone resorption (breakdown) in patients with cancer and in preventing excessive loss of calcium from bone. In cancer-related hypercalcemia, the release of bone-resorbing substances from the tumor (such as parathyroid-related peptide) is responsible for causing bone resorption and calcium ion release from bone and is the proximal cause of disordered calcium homeostasis. Gallium nitrate has previously been shown to inhibit osteoclastic resorption. Warrell et al., "Gallium Nitrate Inhibits Calcium Resorption from Bone and is Effective Treatment for Cancer Related Hypercalcemia", J. Clin. Invest., 73:1487–1490 (1984); Warrell and Bockman, U.S. Pat. No. 4,529,593; and Bockman and Warrell, U.S. Pat. Nos. 4,686,104 and 4,704,277. Early U.S. patents describe methods for preventing the breakdown of bone and disorders of calcium homeostasis that result from the excessive release of bone calcium from the mineralized matrix of bone.

Since the original observations of the antiresorptive activity of gallium, new studies have been undertaken to determine the effects of group IIIa element-containing compounds on osteoblast function with regard to the formation of the organic components of bone. It has now been found that group IIIa element-containing compounds induce osteoblastic cells to synthesize bone matrix components in a manner that mimics the beneficial action of TGFβ. This effect is unique to group IIIa element-containing compounds and not other metals, near metals or antiresorptive compounds. In fact, two metals (zinc and iron) appear to increase the levels of proteins associated with bone breakdown.

With respect to bone mineral breakdown and calcium homeostasis, the actions of gallium nitrate are unrelated to those of TGFβ. Cancer related hypercalcemia and other disorders of calcium homeostasis represent biologic processes that involve bone breakdown, specifically of the mineral matrix, whereas the actions of TGFβ affect bone formation.

Unlike the related chemotherapeutic agents cisplatin or mithramycin, gallium nitrate inhibits resorption without being cytotoxic to osteoclasts. Gallium appears rather subtly to alter the biochemical function of osteoclasts, rendering them less able to dissolve the bone matrices. These processes involve bone breakdown with regard to the mineral matrix but teach nothing about bone formation of the organic matrix and osteoblast formation for repair, healing and augmentation. While preventing bone dissolution may preserve existing skeletal mass, it is not as beneficial as increasing the synthesis of new organic components needed for new, normal, bone formation, repair, healing or augmentation especially when skeletal mass is already inadequate and at risk of fracture or tear. New bone matrix formation is essential to repair and heal existing fractures, augment the organic mass of bone and to help affix bone grafts and prosthetic devices that are placed in bone to maintain or increase bone strength and function.

Group IIIa element-containing compounds have now been found to be suitable for use in bone implants. Bone implants include, but are not limited to, bone grafts, dental implants and prosthetic devices. Implants are routinely used by orthopedists to replace damaged or diseased joints and to support or replace weakened, defective or lost bone. Dental implants include both artificial teeth implanted directly into the jawbone and bone implants to repair, heal or augment diseased, damaged or structurally impaired dental bones such as those involved in cleft palates and other congenital disorders. Dentists use implants to improve the structure of bone around teeth, to fill defects, to improve denture retention and to improve tooth implant retention. Bone grafts restore or replace weakened, broken or missing bone mass and promote fracture healing while prosthetic devices restore mechanical strength and function to the skeletal system by replacing diseased or otherwise non-functioning bone.

Successful implantation and function of bone implants depends on bonding of the adjacent bone to the implant. Such bonding requires bone repair by the formation of new matrix components at the interface between the implant and the bone proximate to the implant. Group IIIa element-containing compounds enhance attachment, fixation and stabilization of bone implants by promoting new organic matrix component formation onto the implant. Additionally, placing group IIIa element-containing compounds on particular sites of an implant can enhance bone attachment onto these sites to further enhance stability and function of the implant.

An estimated ten percent of bone and joint prosthetic devices that are placed in people fail to function due to non-bonding of the bone to an implant. The resulting disability often requires reoperation and reimplantation of the device. Group IIIa element-containing compounds are ideal for enhancing new matrix component formation proximate to a prosthetic device. Group IIIa element-containing compounds are stable and can readily be administered topically at the implantation site. Group IIIa element-containing compounds can also be incorporated into a coating on the surface of the prosthetic device. Such coatings may be composed of a polymer that allows slow diffusion of the group IIIa element-containing compounds at a rate sufficient to enhance bone attachment for a suitable period of time. Suitable coatings include, but are not limited to, hydroxyapatite, methacrylate and tricalcium phosphate. Further, the polymeric coatings can be applied only to the sites on the prosthetic device where bony ingrowth is desired. Bone grafts can be coated with or soaked or immersed in a rinse or gel prior to implantation so as to impregnate the graft with the group IIIa element-containing compound. Topical or local administration of the group IIIa element-containing compounds to either the site of implantation or the implant itself, is preferred, as it diminishes drug exposure for tissues and organs not requiring treatment. For enhancing integration of bone and joint implants, group IIIa element-containing compounds can also be administered parenterally, gastrointestinally, transbronchially or transalveolarly.

Five to ten percent of all bone fractures are never repaired. Although many methods have been proposed to cure these non-healing bone fractures, none has yet proven to be satisfactory. Group IIIa element-containing compounds have now been found to be suitable for treatment of all bone fractures, breaks and tears and are especially suitable for treatment of bone fractures that exhibit delayed repair; where healing is impaired as a consequence of inadequate bone matrix component formation at the site of injury.

In order to achieve enhanced normal healing of bone, the present invention provides compositions for administering therapeutically effective levels of group IIIa element-containing compounds to the affected area either in a topical ointment, rinse or gel or by placement of an implant impregnated with a group IIIa element-containing compound proximate to the site of injury. Alternatively, suitable levels of a group IIIa element-containing compound can be provided to the affected area systemically for instance by parenteral, gastrointestinal, transbronchial or transalveolar administration.

The present invention further provides implants composed of bone or bone matrix, collagen or a polymer impregnated or coated with group IIIa element-containing compounds.

Inadequate organic matrix mass places an individual at risk of skeletal failure such that bone fractures can result from the minimal trauma of everyday life. Such fractures cause significant illness, or morbidity, inasmuch as there is insufficient repair or healing of the fractures. Group IIIa element-containing compounds can prevent such fractures by augmenting the normal organic matrix thereby increasing skeletal mass as well as promoting repair and healing of fractures that occur as a result of reduced skeletal mass. In treatment of patients with inadequate organic bone matrix and at increased risk of bone tears, breaks or fractures, preferred routes of administration include parenteral and gastrointestinal, although transbronchial or transalveolar administration routes are also suitable. In treatment of such patients who have suffered a tear, break or fracture, the methods of administration would be the same as those of other patients with tears, breaks or fractures as described above.

It has now been found that, in bone, group IIIa element-containing compounds not only enhance repair of fractures and tears and promote bone matrix synthesis so as to facilitate incorporation of implants such as bone grafts and prosthetic devices, but also enhance new formation of normal bone matrix in individuals with decreased organic matrix mass so as to prevent fractures, breaks, and tears. Group IIIa element-containing compounds enhance matrix component formation so as to promote repair healing and augmentation to facilitate incorporation of grafts and fix and stabilize prosthetic devices.

Cartilage

It has now been found that, in cartilage, group IIIa element-containing compounds not only enhance repair of fractures and tears, but also promote cartilage matrix synthesis so as to facilitate incorporation cartilage grafts and prosthetic devices. Group IIIa element-containing compounds enhance matrix component formation so as to promote repair healing and augmentation to facilitate incorporation of grafts and fix and stabilize prosthetic devices.

Cartilage is tissue made up of extracellular matrix primarily comprised of the organic compounds collagen, hyaluronic acid (a proteoglycan) and a few cells, chondrocytes, responsible for producing cartilage. No neural, lymphatic or vascular tissue is normally found within cartilage. Collagen, hyaluronic acid and water entrapped within these organic matrix elements yield the unique elastic properties and strength of cartilage. Chondrocytes produce both Type I and Type II collagens. Type II collagen is not found in bone whereas Type I collagen is found in bone and skin. It has previously been shown that the endogenous growth factors TGF$\beta$ and BMP induce both new cartilage and bone formation. Wozney et al. (1988) and Sporn et al. (1987).

In cartilage, collagen synthesis is required for repair, healing and augmentation; as well as for the successful bonding of grafts and prosthetic devices. Collagen is the major structural protein responsible for the architectural integrity of cartilage. Other, noncollagen proteins, such as osteonectin, fibronectin and proteoglycans are also important for cartilage repair.

Cells such as synoviocytes that are found in joint spaces adjacent to cartilage have an important role in cartilage metabolism. Synoviocytes produce metallo-proteinases, such as collagenases that are capable of breaking-down cartilage. TGF$\beta$ is known to inhibit cell-release (and probably synthesis) of metallo-proteinases. Sporn et al. (1987). It has now been found that group IIIa element-containing compounds mimic the activity of TGF$\beta$ to induce chondrocytes (cartilage forming cells) to produce new matrix components and inhibit production of cartilage destructive enzymes so as to effect cartilage repair, healing and augmentation.

Group IIIa element-containing compounds have now been found to be useful in the art of cartilage implants. Cartilage implants are often used in reconstructive or plastic surgery such as rhinoplasty. The present invention provides implants useful for cartilage repair including but not limited to cartilage grafts, and tissue implants such as tendon, ligaments and fascia grafts. The grafts can be selectively coated with compositions for topical application containing therapeutically effective levels of group IIIa element-containing compounds or impregnated by soaking or immersion in solutions of group IIIa element-containing compounds prior to their implantation. Healing of cartilage grafts can also be facilitated by systemic administration of group IIIa element-containing compounds such as parenterally, gastrointestinally, transalveolarly, or transbronchially.

Skin

In skin, as in bone, it has now been found that group IIIa element-containing compounds mimic the effects of TGF$\beta$, a factor identified as an important agent in repair, healing and augmentation of skin. Sporn et al., (1987). Group IIIa element-containing compounds have now been found not only to mimic the effect of TGF$\beta$ in bone but also to mimic the effect of TGF$\beta$ in skin by the synthesis of proteins associated with repair and healing, even in the absence of a specific wound. Group IIIa element-containing compounds, by virtue of their ability to mimic natural growth factors found in bone and skin, are suitable for use in inducing the formation of the matrix elements of skin and thus in increasing the strength of skin as well as repairing specific injuries (wounds) to such tissues.

Repair and healing of skin is another example of organ repair. Similar to bone repair, healing and augmentation of skin involves the production of critical matrix components that form the architectural and structural lattice of skin. The major matrix component is Type I collagen, similar to the case in bone. In skin, fibroblasts synthesize and release new collagen into a wound site. Unlike bone, this matrix is not mineralized. Other proteins produced by fibroblasts contribute to the matrix. One such protein, fibronectin, is thought to function as an important anchoring protein, helping to bind key cells to the underlying matrix. A second skin cell, the keratinocyte, is important in repair and healing of wounds and skin defects. Both the fibroblast and keratinocyte produce fibronectin. Collagen and fibronectin synthesis is enhanced during repair, healing and augmentation of skin. It has now been found that group IIIa element-containing compounds, like TGFβ, induce keratinocytes to produce fibronectin.

The present invention includes various therapeutic compositions for treatment of wounds. These compositions comprise group IIIa element-containing compounds and a pharmaceutically acceptable vehicle. Suitable vehicles for administration of group IIIa element-containing compounds include but are not limited to ointments, creams, gels and rinses into which group IIIa element-containing compounds can be admixed and dissolved in an amount sufficient to be therapeutically effective. Dressings, bandages or other such coverings capable of releasing a therapeutically effective amount of group IIIa element-containing compounds to the wound site are also provided.

In addition to the uses in wound repair, group IIIa element-containing compounds have many dermatologic and cosmetic uses. Increasing production of the connective matrix components facilitates repair and healing of tears, breaks or defects in skin. Increased matrix synthesis increases skin thickness (augmentation), thereby removing wrinkles due to aging and diminishes the consequences of aging. Matrix synthesis induced by group IIIa element-containing compounds selectively fills lines due to aging or skin defects due to prior injury, such as from acne, previous trauma, ultraviolet damage, burns and hereditary and acquired disorders of the skin.

It has now been found that group IIIa element-containing compounds may be topically applied to the skin to treat lines, wrinkles or skin defects. Currently, lines, wrinkles, or skin defects due to ultraviolet exposure, aging, hereditary or acquired skin disorders, acne or other trauma are treated with subcutaneous collagen injections. The collagen, obtained from bovine preparations, is injected directly into the area to be filled. There are certain drawbacks to collagen injections, primarily the possibility of an immediate or long-term immunological response. An immediate immunological response results in swelling, discomfort and lack of aesthetic appeal. Long-term immunological reactions may occur with repeated use resulting in immunological rejection of continued injections.

Additionally, methods are disclosed in the present invention whereby therapeutically effective amounts of group IIIa element-containing compounds are subcutaneously injected directly to the area to be filled-in. Direct injection of group IIIa element-containing compounds results in localized synthesis of native collagen, without either immediate or long-term immunological response. Group IIIa element-containing compounds are thus preferred over collagen injections for filling-in lines, wrinkles or skin defects.

The present invention further includes suitable compositions for topical application and for direct injection into lines, wrinkles or skin defects due to acne or other trauma for the purpose of inducing synthesis of native collagen. Compositions containing a pharmaceutically acceptable vehicle and group IIIa element-containing compounds suitable for topical application include but are not limited to, pharmaceutically acceptable lotions, creams, rinses, gels and liposome carriers suspended in a suitable vehicle. Compositions of group IIIa element-containing compounds for direct injection include, but are not limited to, group IIIa element-containing compounds admixed with pharmaceutically acceptable sterile isotonic solutions, including, but not limited to, saline, phosphate buffered saline and liposomal carrier preparations suspended in a suitable vehicle.

Group IIIa element-containing compounds have now been found to be useful in skin grafts and in the fixation of implants in skin. Treatment of skin grafts with group IIIa element-containing compounds enhances the synthesis of skin matrix components needed for the attachment and fixation of skin grafts and of prosthetic devices into the skin.

The present invention includes skin grafts and implants impregnated or coated with a therapeutically effective amount of group IIIa element-containing compounds. These skin grafts are immersed in a solution, containing a therapeutically effective amount of group IIIa element-containing compounds, for a time sufficient to either coat the graft or allow impregnation of the graft with the group IIIa element-containing compound. The area of the skin to receive the graft or implant can be treated topically with a composition containing a therapeutically effective amount of group IIIa element-containing compounds as described above.

Connective and Support Tissue

Group IIIa element-containing compounds have now been found to be useful in the treatment of wounds in connective and support tissue. Such tissues include, but are not limited to, ligaments, tendons, fascia and collagen containing tissues that encapsulate organs. Collagen containing tissues that encapsulate organs include, but are not limited to, the renal and liver capsules, the meninges, the pericardium and the pleura. The so-called soft tissues of skin, muscle and organs are supported by a collagen containing connective tissue known as fascia, which contributes to the structural integrity and wound healing of these tissues.

In treatment of injury to connective and support tissue, administration of group IIIa element-containing compounds proximate to the wound is preferred. In treatment of injuries to tendon, ligament and collagen containing tissues that encapsulate organs, pharmaceutically acceptable topical and transdermal application of group IIIa element-containing compounds are preferred. Adequate levels of group IIIa element-containing compounds can also be obtained by systemic administration such as parenteral, gastrointestinal, transbronchial or transalveolar.

The present invention provides various therapeutic compositions for treatment of connective and support tissue with group IIIa element-containing compounds. Suitable compositions of group IIIa element-containing compounds include, but are not limited to, pharmaceutically acceptable topical ointments, creams, gels and rinses. Dressings, bandages or other such coverings capable of releasing a therapeutic amount of group IIIa element-containing compound to the wound site are also disclosed. Compositions of group IIIa element-containing compounds suitable for systemic administration include, but are not limited to, pharmaceutically acceptable sterile isotonic solutions, including, but not limited to, saline, phosphate buffered saline and liposomal carrier preparations suspended in a suitable vehicle.

Additionally, the present invention includes tendon, ligament, fascia and grafts to treat torn or damaged tissue. These grafts can be coated or impregnated with therapeutically effective amounts of group IIIa element-containing compounds, by soaking or immersing the grafts prior to implantation, in a pharmaceutically acceptable vehicle containing group IIIa element-containing compounds.

Topical administration of group IIIa element-containing compounds to the site at which the graft is placed is also useful to promote incorporation of tendon, ligament and fascia grafts into adjacent tissues. As with bone implants, the group IIIa element-containing compounds induce matrix component synthesis to enhance attachment, fixation and stabilization of implants by promoting new tissue growth onto the implant.

The present invention is further illustrated by the following specific examples, which are not intended in any way to limit the scope of the invention.

The terms and expressions employed herein are used as terms of description and not of limitation, and there is no intention in the use of such terms and expressions of excluding any equivalents of the features shown and described or portions thereof. While the preferred and alternative embodiments of the invention have been described in detail, it is to be expressly understood that variations and modifications thereof may be carried out by one skilled in the art without departing from the spirit and scope of this invention.

EXAMPLE 1

Group IIIa Element-Containing Compounds Enhance the de novo Formation of Collagen, and Decrease Osteocalcin Synthesis, Key Structural Matrix Proteins To test the effects of group IIIa elements on matrix component synthesis, the levels of two matrix proteins were measured in organ culture and in isolated cells. Two specific matrix proteins, type I collagen and osteocalcin (also known as Gla protein), were chosen because they reflect whether repair or breakdown were predominant. Type I collagen is the major matrix protein of bone, skin, connective and support tissue. New collagen synthesis was measured in a normal organ culture system, newborn rat calvarial explants. Osteocalcin is a bone-specific matrix protein. Osteocalcin is thought to be a cell signal for attracting osteoclasts to bone so as to initiate bone breakdown. Osteocalcin is also thought to slow or impede formation of newly mineralizing bone. Price et al., "Excessive Mineralization with Growth Plate Closure in Rats on Chronic Warfarin Treatment", Proc. Natl. Acad. Sci. USA, 79:7734–7738 (1982). Therefore, decreased osteocalcin synthesis is associated with bone repair, healing or augmentation. The results showed that group IIIa element-containing compounds enhance the de novo formation of collagen, and decrease osteocalcin synthesis.

New collagen synthesis is an excellent biochemical marker to indicate whether the new matrix components necessary for repair, healing and tissue augmentation are being synthesized. However, to prove that the cellular program of repair, healing and augmentation is occurring, a broader panel of matrix protein expression must be studied (see Example 2). Osteocalcin synthesis in response to gallium nitrate was followed in the rat osteoblastic cell line (ROS 17/2.8, hereinafter, "ROS cells"). Majeska et al., "Parathyroid Hormone: Responsive Clonal Cell Lines from Rat Osteosarcoma", Endocrinol., 107:1494–1503 (1980).

The results obtained show that gallium nitrate increases the levels of proline (Pro) and hydroxyproline (OH-Pro) in fetal rat hemicalvaria and decreases the levels of osteocalcin in an osteoblast cell line. In fact, gallium inhibits the ability of Vitamin $D_3$ to increase osteocalcin levels in the osteoblast cell line.

Calvarial (skull) bones from newborn rats were placed in sterile culture dishes with a nutritive media to maintain viability. In this state, structural tissues grow by forming new matrix components (notably bone-specific collagen), but this growth is very slow. Kream et al., "Characterization of the Effect of Insulin on Collagen Synthesis in Fetal Rat Bone", Endocrinol., 116:296–302 (1985). Collagen is a unique protein, being almost entirely composed of Pro, OH-Pro, alanine and glycine. New bone-collagen synthesis was determined by measuring the uptake of $[^3H]$-Pro or by following the appearance of $[^3H]$-OH-Pro, which is formed by conversion of proline subsequent to its incorporation into collagen.

Hemicalvaria from 21 day old fetal rats were incubated for 48 hours in the presence and absence of gallium nitrate at various concentrations as listed in Table 1. $[^3H]$-Pro was added for the last 18 hours of the incubation.

The results obtained are presented in Table 1. The data are reported as counts per minute of $[^3H]$ per mg bone (cpm/mg). With the addition of gallium nitrate at the therapeutic doses, a two-to-three fold enhancement in collagen synthesis, over controls, was measured.

TABLE 1

| Treatment | Pro | OH-Pro |
| --- | --- | --- |
| Control | 40,457 ± 12,680 | 5,498 ± 1924 |
| Gallium | | |
| 50 µM | 61,845 ± 26,076 | 10,373 ± 2916 |
| 100 µM | 76,450 ± 33,210 | 12,763 ± 5250 |

It is known that this new collagen can be mineralized as evidenced by the increased uptake of $[^{45}Ca]$ into newly formed bone matrix. Repo et al., "Effect of Gallium on Bone Mineral Properties", Calcif. Tissue Int., 43:300–306 (1988). Therefore, one can conclude that the collagen synthesis induced by gallium is normal with regard to this important functional parameter.

Repair, healing and augmentation of organs and tissues are complicated processes. A favorable change in one component (collagen) does not teach that the biologic processes of repair, healing and augmentation will occur. To be effective agents and factors that induce these processes must initiate a program of matrix protein synthesis. To show that a specific pattern of protein synthesis could be induced by group IIIa element-containing compounds, osteocalcin synthesis by an osteoblast cell line was examined.

Osteocalcin is thought to slow or impede the formation of newly mineralizing bone. Osteocalcin is also thought to slow or impede formation of newly mineralizing bone. Price et al. (1982). Therefore, a decrease in osteocalcin would be expected to benefit bone formation. Noda and Rodan, Ibid.

To determine if the increase in Type 1 collagen that was noted with exposure of cells to gallium nitrate (Table 1) was correlated with a concomitant decrease in osteocalcin protein levels, osteocalcin protein levels were measured in the culture media of the osteoblast cells after gallium nitrate treatment.

Osteocalcin levels released by osteoblasts were measured using a radioimmunoassay specific for osteocalcin. The radioimmunoassay was provided by Biomedical Technologies Inc., Stoughton, Mass. (BTI) and used according to the manufacturer's instructions. The levels of osteocalcin normally produced in osteoblast cells were compared to osteocalcin levels in identical cells exposed to gallium nitrate. The results obtained are shown in Table 2. ROS cells grown to confluence in HAM's F-12 plus 10% newborn calf serum were untreated or treated with either 50 µM gallium nitrate, 2.5 nM 1,25-dihydroxyvitamin $D_3$, or both for 96 hours. Media were aspirated and assayed for osteocalcin. Values are expressed as nanograms/$10^6$ cells and N=6, the number of dishes assayed. The results obtained indicate that the experimental cells were highly significant compared to control cells (p<0.005) and from Vitamin $D_3$ (p<0.01) by student-t test.

TABLE 2

Osteocalcin Levels Released by Osteoblasts

| Treatment | Osteocalcin (ng/ml) |
| --- | --- |
| Control | 426 ± 52 |
| Gallium | 255 ± 53 |
| Vitamin $D_3$ | 1073 ± 252 |
| Gallium + Vitamin $D_3$ | 554 ± 289 |

The results depicted in Table 2 show that the levels of osteocalcin fell after gallium nitrate treatment, confirming the correlation of a decrease in the production of osteocalcin at a time when collagen synthesis increased. Further, gallium nitrate reduces Vitamin $D_3$-stimulated osteocalcin protein levels.

The decrease in osteocalcin levels induced by gallium nitrate is similar to the effects seen with the naturally occurring growth factor TGFβ normally found in bone and known to enhance matrix formation.

EXAMPLE 2

Group IIIa Element-Containing Compounds Induce Matrix Gene Expression by Cells Derived from Bone, Skin and Connective and Support Tissues To ascertain the specificity of group IIIa element-containing compounds, and compare the compounds to TGFβ, a variety of cell types were administered several metal and near metal containing compounds, gallium nitrate, indium nitrate, TGFβ or selected bisphosphonate compounds. The cells were then assayed for the presence of mRNA encoding α-1 procollagen, osteocalcin, osteonectin, osteopontin, fibronectin, and α-actin. Like collagen, fibronectin is an important matrix protein, the increased synthesis of which is usually an indicator of increased matrix formation. The results obtained showed that only the group IIIa elements mimic the mRNA changes obtained when these same cells are exposed to TGFβ. Surprisingly, both ferric chloride and zinc chloride caused approximately two- to three-fold elevated levels of osteocalcin mRNA, an effect opposite to that of gallium, indium and TGFβ. The results showed that group IIIa element-containing compounds induce matrix gene expression by cells derived from bone, skin and connective and support tissues.

The results obtained in Example 2 show that group IIIa elements specifically increase the expression of mRNA encoding structural matrix proteins in cells derived from bone and cartilage, skin and connective and support tissues. Other matrix proteins, such as osteopontin were unchanged or decreased (osteocalcin). The pattern of mRNA synthesis induced by group IIIa element-containing compounds is one consistent with production of new matrix proteins that are specially required to repair, heal and augment bone, cartilage, skin and connective and support tissues.

Treatment of the human keratinocytes and fibroblasts with increasing amounts of gallium also resulted in a dose-dependent increase of fibronectin and collagen mRNA. The effects of group IIIa elements on osteoblasts, keratinocytes, and fibroblasts thus mimic those reported for TGFβ. The results shown are of particular interest in that primary, diploid, non-transformed cells demonstrate the same response to group IIIa element-containing compounds as the transformed ROS cell line. This indicates that the ability of group IIIa element-containing compounds to alter matrix protein mRNA levels is not restricted to transformed osteoblastic cells and that matrix protein genes in other types of mesenchymally-derived cells may be regulated in a similar manner.

The cell lines used in this study include human skin fibroblasts, human skin keratinocytes, a clonal mouse osteoblast cell line (MC3T3-E1), mouse fibroblasts (NIH 3T3), rabbit synoviocytes (HIG-82, a cartilage cell) and ROS cells. The fibroblasts and keratinocytes are primary cultures derived from human skin. The clonal mouse cell line (MC3T3-E1) and the rat osteosarcoma cell line are permanent cell lines that maintain many of the characteristics of osteoblasts. Kumegawa et al., "Effects of Epidermal Growth Factor on Osteoblastic Cells in vitro", Calcif. Tis. Int., 35:542–548, (1983); and Majeska et al. (1980). The cell line HIG-82, is a permanent cartilage cell line which retains many features present in normal synoviocytes. Georgescu et al., "HIG-82: An Established Cell Line From Rabbit Periarticular Soft Tissue, Which Retains the "Activatable" Phenotype", in vitro Cell. Dev. Biol., 24:1015–1022 (1988).

The metal and near metal compounds included ferric nitrate, ferric chloride, ferrous chloride, aluminum chloride, zinc chloride, cisplatin and spirogermanium, and the group IIIa elements, gallium nitrate and indium nitrate. The metal and near metal compounds were tested at 50 µM. The selected bisphosphonates included etidronate (EHDP) and clodronate ($Cl_2MDP$) and were administered at concentrations known to elicit antiresorptive activity. TGFβ (Gibco/BRL, Grand Island, N.Y.) was tested at 5 ng/ml.

The fibroblasts, keratinocytes, synoviocytes and osteoblasts were exposed to the compounds for 24–48 hours, after which total cellular RNA was isolated by guanidinium isothiocyanate extraction and ultracentrifugation through cesium chloride according to the method described by Chirgwin et al., "Isolation of Biologically Active Ribonucleic Acid from Sources Enriched in Ribonuclease", Biochem., 18:5294–5299 (1979). The RNA was separated by electrophoresis on a denaturing MOPS-formaldehyde agarose gel (Biorad Products, Rockville Center, N.Y.), transferred to Nytran filters (Schleicher and Schuell, Keane, N.H.), and hybridized with [$^{32}P$]dCTP (New England Nuclear) labeled cDNA probes specific for the matrix proteins. The cDNA probes included: α-1 procollagen; osteocalcin; osteonectin; osteopontin; fibronectin; and the constitutively synthesized protein α-actin as an internal control. Radiolabeling of the probes was done according to the random priming method described by Feinberg et al., "A Technique for Radiolabeling DNA Restriction Endonuclease Fragments to High Specific Activity", Anal. Biochem., 132:6–13 (1983).

The cDNA probes were obtained from Drs.: David Rowe (procollagen, University of Connecticut, Storrs, Conn.); P. Robey (osteopontin, osteonectin, National Institutes of Health, Bethesda, Md.); John Wozney (osteocalcin, Genetics Institute, Cambridge Park, Mass.); Dr. R. Hynes (fibronectin, Cambridge, Mass.) and Lydia Pan (α-actin, Stanford, Palo Alto, Calif.). Hybridization of the probes to the filters was performed according to the manufacturer's instructions (Schleicher and Schuell). The hybridized filters (Northern blots) were washed under stringent conditions and exposed to X-ray film.

After developing the X-ray film, the bands corresponding to procollagen, osteopontin, osteocalcin and α-actin mRNA'S were scanned using an LKB Model 2202 Ultroscan Laser densitometer to provide an estimate of the percent change in mRNA levels after gallium nitrate treatment and the results were compared to those obtained from control cells not treated with gallium nitrate. The results are shown in Table 3 where the numbers represent the percent change in treated cells compared to untreated cells.

The results listed in Table 3 show that only TGFβ and the group IIIa element gallium cause an increase in α-1 procollagen mRNA and both gallium and indium caused a decrease in osteocalcin mRNA.

EXAMPLE 3

Cellular Actions of Group IIIa Element-Containing Compounds Are Effected at the Transcriptional Level The results obtained in Examples 1 and 2 indicate that the cellular mechanisms responsible for the group IIIa element-containing compound induced changes occur at the level of gene expression. While the level of mRNA transcription is regulated, the effect is not due to regulation of mRNA stability. The results described below support this theory by showing that treatment of cells with gallium nitrate does not affect osteocalcin mRNA stability. If group IIIa element-containing compounds caused a more rapid breakdown of osteocalcin mRNA, then one would anticipate that less osteocalcin would be measured and less mRNA would be seen on the Northern blots. Using the RNA polymerase II inhibitor 5,6-dichloro-1-β-D-ribofuranosylbenzimidazole (DRB), it was found that the decay in measurable osteocalcin mRNA was not different in the untreated and gallium-treated cells. Therefore, there is no evidence that group IIIa element-containing compounds alter mRNA stability.

To more clearly demonstrate that the "direct" effect of group IIIa element-containing compounds is on gene expression, gene transfer experiments were initiated. Unless otherwise indicated, molecular biology techniques used are those described in Sambrook et al., *Molecular Cloning*, 2nd ed, Cold Spring Harbor Laboratory Press, N.Y. (1989).

A plasmid (pCOLCAT) containing a 3.6 kb DNA fragment encoding 5'-flanking DNA of the rat α1(I) collagen

TABLE 3

PERCENT CHANGE IN MATRIX PROTEIN
mRNA LEVELS AFTER GROUP IIIa TREATMENT

| mRNA Source | Group IIIa | | | Other Metals | | Bisphosphonates | |
| --- | --- | --- | --- | --- | --- | --- | --- |
| | Gallium Nitrate | Indium Nitrate | TGFβ | Zinc Cl | Ferric Cl | EHDP | Cl₂ MDP |
| OSTEOBLAST | | | | | | | |
| α1(I) Collagen | +150 | | +160 | | | | |
| Osteopontin | 0 | | +70 | | | | |
| Osteocalcin | −40 | −50 | −50 | +270 | +180 | 0 | 0 |
| α-Actin | +10 | | | | | | |
| FIBROBLASTS | | | | | | | |
| α1(I)Collagen | +200 | | +200 | | | | |
| KERATINOCYTES | | | | | | | |
| α-Actin | +50 | | +250 | | | | |
| Fibronectin | +150 | | +250 | | | | |

Thus, the group IIIa elements, such as gallium and indium, but not other metal- or near metal-containing compounds or bisphosphonates, modulate the synthesis of mRNA encoding key stromal matrix components. There was no evidence of an increase in TGFβ activity in the culture media of cells exposed to gallium nitrate, showing that the matrix enhancing effect was directly mediated by gallium or indium nitrate, not indirectly through induction of endogenous TGFβ synthesis. Additionally, several other metals (iron and zinc) appear to induce production of osteocalcin mRNA which would be expected to result in enhancing matrix breakdown.

gene promoter linked to the reporter gene chloramphenicol acetyltransferase (CAT) putting CAT expression under control of the rat α(I) collagen promoter was provided by Dr. D. Rowe, U. Connecticut Medical Center, Farmington, Conn. A 0.9 kb DNA fragment containing 5'-flanking region DNA of the mouse α1(I) collagen gene promoter (MCOL/CAT) was provided by Dr. B. de Crombrugghe Univ. of Texas, M.D. Anderson Cancer Center, Houston, Tex. A plasmid (pBGPCAT) containing a 2.0 kb fragment of DNA sequences upstream from the start site of transcription of the rat osteocalcin gene linked to CAT was provided by Dr. M. Demay, Massachusetts General Hospital, Boston, Mass. Portions of each of the three 5'-flanking regions were excised and cloned into pZLUC, a plasmid obtained from Dr. P. Deutsch (Cornell U. Medical College, New York, N.Y.) which contains the luciferase reporter gene cloned into a derivative of the plasmid vector pUC18 so as to put the luciferase gene under control of each of the three promoters respectively. Luciferase was chosen as the reporter gene since the luciferase protein assay is far more sensitive than the CAT assay and takes less time to perform.

In a preliminary study using the 0.9 kb mouse 5'-flanking region of the α1(I) collagen gene cloned into pZLUC, ROS cells approximately 80% confluent were transfected using the calcium phosphate precipitation method. 24 hours after transfection, cells were treated with either TGFβ (1–5 ng/ml) or gallium nitrate (10–100 μM), incubated for 24 hours and assayed for luciferase activity according to the method described by Deutsch et al, "Vasoactive Intestinal Peptide Increases Intracellular cAMP and Gondotropin-α Gene Activity in JEG-3 Syncytial Trophoblasts", J. Biol. Chem., 265:10279–10281 (1990). To ensure reproducibility, all transfections were done in triplicate. As seen in Table 4, treatment of cells transfected with the 0.9 kb mouse α1(I) collagen promoter showed a 1.5-fold increase in luciferase activity when treated with either TGFβ or gallium nitrate compared to untreated cells. These results show that group IIIa element-containing compounds directly activate α1(I) collagen mRNA transcription.

TABLE 4

| Treatment | Luciferase Activity (in Thousands of Relative Light Units) |
| --- | --- |
| Control | 104.4 |
| TGFβ | 145 |
| Gallium | |
| 25 μM | 146 |
| 100 μM | 94 |

Studies with stably transfected cells have also been carried out. These cells, received from Dr. D. Rowe, are ROS cells which have been cotransfected with pCOLCAT and a RSV-neomycin G418 resistance plasmid. Several hundred G418-resistant colonies were pooled and designated 3.6COLCAT/RSVNEO. These cells were treated with either gallium nitrate (10–100 μM) or TGFβ (1–5 ng/ml) and assayed for CAT activity 24 hours later according to the method of Deutsch et al., (1990). The results are shown in Table 5.

Treatment of 3.6COLCAT/RSVNEO with gallium nitrate stimulated CAT activity 2.5-fold higher than untreated cells (Table 5), a result which confirms the finding that gallium nitrate directly activates α1(I) collagen gene expression.

TABLE 5

| Treatment | cpm |
| --- | --- |
| Control | 26.4 |
| TGFβ | 54.6 |
| Gallium | |
| 10 μM | 41.0 |
| 100 μM | 61.0 |

EXAMPLE 4

Early Protein Synthesis is Required for the Action of Group IIIa Element-Containing Compounds; Expression of Two Classes of Cellular Proteins is Affected It was of interest to determine whether the group IIIa element-containing compound mediated inhibition of osteocalcin transcription and whether stimulation of α1(I) collagen mRNA transcription requires new protein synthesis. The studies presented here show that group IIIa element-containing compounds, like TGFβ, inhibit basal and vitamin $D_3$-stimulated osteocalcin transcription and stimulate α1(I) collagen gene expression, a pattern thought to be consistent with that of new matrix component formation necessary for repair, healing and augmentation of bone and cartilage, skin and connective and support tissue. These effects are virtally unique to group IIIa element-containing compounds compared to iron, zinc, magnesium and several other metal and near-metal salts examined. New protein synthesis is required for these effects to be seen, and at least one nuclear regulatory protein has been identified whose synthesis is stimulated by both group IIIa element-containing compounds and TGFβ: the product of the proto-oncogene c-fos.

Group IIIa element-containing compounds are able to directly stimulate α1(I) collagen gene expression as assayed by both transiently and stably transfected cell lines. From such data, it is evident that group IIIa element-containing compounds affect cells by previously unknown complex actions. Group IIIa element-containing compounds, like several recently described natural factors that can induce tissue repair, regulate both early (c-fos) and late (α1(I) collagen and osteocalcin) gene expression. These studies provide important insights into the molecular events required for regulation of matrix component expression; the very events that are necessary for bone and cartilage, skin and connective and support tissue repair, healing and augmentation.

Gallium nitrate was added to ROS cells in the presence or absence of 2 μg/ml of the protein synthesis inhibitor cycloheximide (Sigma Chemical Co., St. Louis, Mo.), a concentration that inhibits new protein synthesis by approximately 90%. 24 hours after addition of cycloheximide, total RNA was harvested according to the method described by Chirgwin et al. (1979) and subjected to Northern blot analysis as described in Example 2. The results obtained indicate that in the presence of cycloheximide, gallium nitrate does not cause the usual reduction in osteocalcin mRNA or stimulation of α1(I) collagen mRNA levels. These results suggest that group IIIa elements require protein synthesis in order to suppress osteocalcin or to stimulate α1(I) collagen gene transcription. It is also unlikely that group IIIa elements act directly on the 5'-flanking region of the osteocalcin gene. Instead, a protein synthesized in response to group IIIa element treatment most probably mediates their regulatory effects on osteocalcin and α1(I) collagen gene transcription.

Several interesting phenomena have now been observed with regard to molecular changes caused by group IIIa elements. It has now been found that gallium decreases osteocalcin transcription and increases α1(I) collagen gene expression in several different cell types, but does not affect expression of other genes, such as osteopontin or actin. Moreover, gallium requires protein synthesis to exert its affects on gene expression. Studies were conducted to investigate whether gallium nitrate might affect one or more early regulatory genes or their protein products which would in turn mediate the changes in gene expression mentioned above.

The transcription factor Fos was initially examined as the possible link between gallium and its nuclear effects for the following reasons: 1) the c-fos gene is the proto-oncogene equivalent of v-fos, an oncogene well known for its ability to induce osteosarcomas (bone-tumors) in newborn mice, and deregulated c-fos expression in transgenic animals produced unique alterations in bone forming tissues, linking the expression of the gene to bone formation; 2) Fos is a component of a complex of transcription factors known as AP-1 (activator protein 1), whose components include members of the jun proto-oncogene family. Combinations of homo and heterodimers between different members of the fos and jun gene families may result in discordant effects on gene transcription; hence the possibility exists that gallium could inhibit osteocalcin mRNA synthesis by stimulating one set of Fos/Jun proteins, while increasing type α1(I) collagen mRNA synthesis via the interaction of another set of Fos/Jun members; 3) AP-1 response elements are known to exist within the promoter sequences of the genes studied in Example 2 (osteocalcin and α1(I) collagen).

To determine if gallium nitrate induces c-fos gene expression, confluent ROS cells were treated with 50 μM gallium for up to 240 minutes. Total RNA was isolated according to the method of Chirgwin et al. (1979). c-fos mRNA could not be detected via Northern blot analysis, consequently, S1 nuclease digestion was used to quantify c-fos mRNA in the gallium treated cells. S1 nuclease was used according to the manufacturer's instructions. (Boehringer Mannheim, Indianapolis Ind.). The S1 nuclease protocol used is described in Ley et al., "RNA Processing Error in Patients with beta-thalassemia", Proc. Natl. Acad. Sci., 79:4775–4779 (1982). The results obtained showed that gallium nitrate induced a rapid yet transient increase in c-fos mRNA levels; by 120 minutes of treatment, a maximal 3.0-fold stimulation of c-fos mRNA was seen.

Although gallium nitrate increases synthesis of c-fos mRNA, the preliminary results presented here do not prove that Fos is a component of the pathway by which the aforementioned effectors may regulate gene expression in mesenchymally-derived cells. Additional data to support a role for Fos as a (the) transcription factor through which group IIIa element-containing compounds work would be obtained by defining the DNA sequence(s) on the rat osteocalcin and α1(I) collagen 5'-flanking regions which are responsive to the effects of group IIIa element-containing compounds.

EXAMPLE 5

Gallium Nitrate Affects Osteoblast Function in vivo

To determine the effect of gallium nitrate on osteoblast function in intact animals, an experimental model was used which reflects abnormal osteoblast activity. Gallium nitrate was analyzed for its ability to restore normal osteoblast activity to the experimental model.

The results obtained from this experiment indicate that in this rat model system treatment with a therapeutically active formulation of group IIIa element-containing compounds results in a normalization of osteoblast cell function with an attendant increase in bone mass.

The model for abnormal osteoblast activity was weanling Sprague-Dawley rats placed on a phosphate and vitamin D-deficient diet as per the manufacturer's instructions (the diet, #80039, Teklad, Madison, Wis.) The animals on the diet were also kept in the dark to prevent de novo vitamin D synthesis. Animals placed under such conditions show abnormal bone formation and a marked deficiency in total bone mass.

One group of the weanling rats on the diet was treated with gallium nitrate at 25 mg/kg, given as a subcutaneous injection, every other day for 21 days. One group on the diet remained untreated and served as the control. Littermate controls not on the diet and not treated with gallium nitrate supplied blood samples at the time of sacrifice of the animals on the diet for determination of alkaline phosphatase activity. Upon sacrifice, the long bones were removed from the animals on the diet for subsequent analyses.

As previously noted, serum alkaline phosphatase activity is used as a reliable indicator of osteoblast activity, such that increased levels of alkaline phosphatase activity are evidence of the abnormal bone turnover in the experimental animals. Serum alkaline phosphatase activity was determined by measuring the hydrolysis of p-nitrophenyl phosphate by serum samples according to the method of Lowry et al., "Histochemistry of Brain", J. Biol. Chem., 207:19–37 (1954).

The results showed that serum alkaline phosphatase activity was markedly elevated in the animals on the diet that were not treated with gallium nitrate; 660±20 units/ml vs 470±40 units/ml for littermate controls not on the diet. By contrast, the animals on the diet treated with gallium nitrate show normalization of bone cell function as evidenced by the lower level of serum alkaline phosphate activity; 250±30 units/ml. Further, the gallium nitrate treated animals showed greater bone mass. Examination of the ash weights of bones from the animals on the diet showed there was a significant increase (2% ±0.5%) in bone mineral in the gallium-treated rats compared to the untreated rats. These results indicate enhanced matrix synthesis during gallium treatment in the intact animal.

EXAMPLE 6

Gallium Nitrate Induces Human Keratinocyte Proliferation

A critical step in wound repair and healing of skin tears and breaks is the re-epithelization of the wound. An initial step in wound healing is the proliferation of specific skin cells known as keratinocytes. These cells grow into a wound from the edges of the wound to provide a protective cellular barrier over the wound. Increasing keratinocyte proliferation means that wound healing is accelerated. The protective barrier over the skin wound is thus established early allowing subsequent healing to proceed in a protected and sterile environment. Wound infection due to inadequate sealing of the wound is probably one of the major impediments to wound healing.

At the present time, the endogenous natural growth factors in skin that can initiate this critical proliferation have not been fully identified.

When freshly isolated human keratinocytes were treated with gallium nitrate, low concentrations of group IIIa element-containing compounds induced a proliferative response. Coupled with known enhancement of fibroblast production of key matrix components, group IIIa element-containing compound treatment of skin wounds greatly facilitates and accelerates wound repair and healing.

Human keratinocytes were prepared from split thickness skin specimens removed from cadavers, according to the method described by Staiano-Coico et al., "Human Keratinocyte Culture", J. Clin. Invest., 77:396–404 (1986). Briefly, the tissue specimens were suspended in sterile Eagle's minimum essential medium containing antibiotics to prevent bacterial and fungal growth. The tissue was placed in phosphate-buffered saline that contained 0.5% trypsin but was calcium and magnesium free, for 90 minutes at 37° C. Single cell suspensions were prepared by the addition of 0.25% DNase I, then fetal calf serum followed by filtration through sterile gauze. The isolated cells were harvested by centrifugation then resuspended in media containing 20% fetal bovine serum supplemented with amino acids, hormones and antibiotics. All reagents and media were obtained from Sigma Chemical Company, St. Louis, Mo.

By measuring keratinocyte cell numbers, it has now been shown that a 10 µM concentration of gallium nitrate was sufficient to produce a doubling in keratinocyte cell number after seven days. The results are shown in Table 6 where the cell count is in the millions and the control is untreated cells.

TABLE 6

| Day of Study | Control | Gallium |
|---|---|---|
| 3 | 3.12 ± 0.58 | 3.45 ± 0.4 |
| 7 | 2.80 ± 0.81 | 5.33 ± 0.15 |

EXAMPLE 7

Gallium Nitrate has a Positive Affect on Wound Repair and Healing in an Animal Model An animal model of superficial (skin) wounds was examined to study the affect of group IIIa element-containing compounds on wound repair and healing. The data indicate that group IIIa element-containing compounds accelerate wound healing.

Split thickness skin wounds, approximately 2×2 cm were made over the back of anesthetized swine according to the method described by Staiano-Coico et al. (1986). The pig model is commonly used in such studies as pig skin is most like human skin. A small amount of a gallium nitrate solution (50 to 100 µl containing 1.25 to 2.5 mg of gallium nitrate) was placed onto 11 wounds and an occlusive adhesive dressing was used to cover the wounds. A placebo solution (saline, 50 to 100 µl) was placed onto each of 11 "mirror", identical wounds which were also covered with occlusive dressing. After 3 days, the animals were anesthetized, sacrificed and full thickness skin samples twice as large as the original skin wound they contained were removed. The samples were coded to blind the treatment received analyzed by a pathologist and scored for the percent of healing. This scoring method predominantly measures the amount of epithelialization (wound coverage by keratinocytes) that had taken place during the 3 days of repair and healing since the wounding, Table 7 shows the results for the 11 wounds treated with gallium nitrate compared to the saline controls expressed as the percent of healing. A higher percent reflects more healing.

TABLE 7

| Wound # | Percent of Healing | |
|---|---|---|
| | Gallium treated | Control (saline) |
| 1 | 50 | 50 |
| 2 | 20 | 60 |
| 3 | 20 | 10 |
| 4 | 95 | 60 |
| 5 | 50 | 25 |
| 6 | 30 | 30 |
| 7 | 70 | 20 |
| 8 | 30 | 60 |
| 9 | 70 | 70 |

TABLE 7-continued

| Wound # | Percent of Healing | |
|---|---|---|
| | Gallium treated | Control (saline) |
| 10 | 80 | 60 |
| 11 | 90 | 50 |

The data show that 6 of the gallium-treated wounds had improved repair and healing, 3 wounds were not different than control and 2 wounds, wounds 2 and 8, were less healed. Compared to previous studies in this pig model, the results with group IIIa element-containing compounds treatment are far superior to most agents tested to date. These studies support the results obtained with the isolated human keratinocytes reported in Example 6 and show that group IIIa element-containing compounds enhance skin repair and healing in an intact living animal, one that is considered to have skin most similar to that of humans.

Various publications are cited herein, the contents of which are hereby incorporated by reference in their entirety.

We claim:

1. A method to enhance attachment, fixation and stabilization of a bone implant comprising administering to a patient to receive the implant an amount of a pharmaceutically acceptable group IIIa element-containing compound sufficient to provide therapeutically effective levels of the element.

2. The method according to claim 1 wherein the element is selected from the group consisting of boron, aluminum, gallium, indium and thallium.

3. The method according to claim 1 wherein the implant is selected from the group consisting of a bone graft, prosthetic device and dental implant.

4. The method according to claim 1 wherein the implant is prepared for implantation by immersing the implant in a solution comprising a therapeutically effective amount of the compound and a pharmaceutically acceptable vehicle for a time sufficient to either coat the graft with the compound or to allow impregnation of the graft with the compound.

5. The method according to claim 1 wherein the compound is a gallium-containing compound selected from the group consisting of gallium nitrate, gallium citrate, gallium phosphate, gallium chloride, gallium fluoride, gallium carbonate, gallium acetate, gallium tartrate, gallium maltol, gallium oxalate, gallium formate, gallium oxide, hydrated gallium oxide and coordination complexes of gallium.

6. The method according to claim 5 wherein the coordination complexes of gallium are selected from the group consisting of gallium pyrones, gallium pyridones, gallium hydroxymates, gallium aminocarboxylates and gallium oximes.

7. The method according to claim 1 wherein the compound is bound to a protein.

8. The method according to claim 7 wherein the protein is transferrin or lactoferrin.

9. The method according to claim 1 wherein the compound is administered to the patient via a route selected from the group consisting of topical, transdermal, parenteral, gastrointestinal, transbronchial and transalveolar.

* * * * *